United States Patent [19]
Valdes et al.

[11] Patent Number: 5,925,340
[45] Date of Patent: Jul. 20, 1999

[54] PEARLESCENT AMPLIFIER FOR SURFACTANTS

[75] Inventors: Arturo Valdes; Anil Shah, both of North Bergen; Marc Blumstein, Hackensack, all of N.J.

[73] Assignee: Henkel Corporation, Gulph Mills, Pa.

[21] Appl. No.: 08/892,711

[22] Filed: Jul. 15, 1997

[51] Int. Cl.$^6$ ...................................................... A61K 7/075
[52] U.S. Cl. .................. 424/70.19; 424/401; 424/70.13; 514/943
[58] Field of Search ................................ 424/401, 70.19, 424/70.31; 514/943

[56] References Cited

U.S. PATENT DOCUMENTS

| Re. 34,584 | 4/1994 | Grote et al. | 252/142 |
| 4,777,038 | 10/1988 | Scheuffgen | 424/70 |

*Primary Examiner*—Thurman K. Page
*Assistant Examiner*—Lakshmi Channavajjala
*Attorney, Agent, or Firm*—Ernest G. Szoke; Wayne C. Jaeschke; Steven J. Trzaska

[57] ABSTRACT

A pearlescent concentrate containing: (a) a pearlescent agent; (b) a cocamide monoethanolamine having a specific carbon chain distribution; and (c) water.

20 Claims, No Drawings

5,925,340

PEARLESCENT AMPLIFIER FOR SURFACTANTS

FIELD OF THE INVENTION

The present invention generally relates to a novel pearlescent concentrate for surfactant systems. More particularly, by employing a monoethanolamide having a specific carbon chain distribution in combination with a pearlescent agent, a concentrate which imparts a deep, rich pearl to surfactant compositions is obtained.

BACKGROUND OF THE INVENTION

Aqueous preparations of surfactants and cosmetic preparations may be given a pearlescent, aesthetically pleasing appearance by incorporation of substances which, after cooling, precipitate in the form of fine crystals resembling mother-of-pearl in appearance and which remain dispersed in the preparations. Known pearlescents include, for example, the mono- and diesters of ethylene glycol, propylene glycol and oligomeric alkylene glycols and also monoalkanolamides of $C_{12-22}$ fatty acids with $C_2$ or $C_3$ alkanolamines.

It is also known that the pearlescents identified above form stable dispersions in water or in aqueous surfactant solutions and that the concentrated pearlescent dispersions obtained in this way may be added without heating the preparations to be pearlized, so that there is no need for the heating and cooling otherwise necessary for incorporation to form the pearlescent crystals.

While known pearlescents perform satisfactorily in providing pearlescent properties to compositions to which they are added, it is oftentimes desirable to further boost/enhance these properties in order to obtain a deeper, richer pearl quality.

SUMMARY OF THE INVENTION

The present invention is directed to a pearlescent concentrate containing:

(a) from about 1 to about 25% by weight of a pearlescent agent;

(b) from about 2 to about 15% by weight of a $C_{8-18}$ monoethanolamide having a carbon chain distribution of:

(i) $C_8$ ranging from about 0.05 to about 2%;
(ii) $C_{10}$ ranging from about 0.1 to about 2%;
(iii) $C_{12}$ ranging from about 40 to about 70%;
(iv) $C_{14}$ ranging from about 15 to about 30%;
(v) $C_{16}$ ranging from about 5 to about 20%;
(vi) $C_{18}$ ranging from about 1.5 to about 5%; and
(vii) $C_{18}$ consisting of a combination of oleic and linoleic acids ranges from about 5 up to 7%; and (c) remainder, water, the weights of (a)–(c) being based on the total weight of the pearlescent concentrate.

The present invention is also directed to a surfactant composition containing at least one surfactant component and from about 10 to about 75% by weight, based on the total weight of the composition, of the above-disclosed pearlescent concentrate.

The present invention is also directed to a process for making a pearlescent surfactant composition involving providing a surfactant composition and adding thereto an effective amount of the above-disclosed pearlescent concentrate.

DESCRIPTION OF THE INVENTION

Other than in the operating examples, or where otherwise indicated, all numbers expressing quantities of ingredients or reaction conditions are to be understood as being modified in all instances by the term "about".

The pearlescent agents which may be employed in the present invention include, but are not limited to, mono- and diesters of ethylene glycol, propylene glycol, oligomeric alkylene glycols and monoalkanolamides of $C_{12-22}$ fatty acids with $C_2$ or $C_3$ alkanolamines. Particularly preferred pearlescent agents for use in the present invention include ethylene glycol mono- and distearate.

The $C_{8-18}$ monoethanolamide, i.e., cocamide monoethanolamine, used in the present invention is derived by reacting a monoethanolamine with a specific $C_{12-18}$ fatty alcohol cut which results in the formation of a cocamide monoethanolamine having a carbon chain distribution corresponding to: (i) $C_8$ ranging from about 0.05 to about 2%; (ii) $C_{10}$ ranging from about 0.1 to about 2%; (iii) $C_{12}$ ranging from about 40 to about 70%; (iv) $C_{14}$ ranging from about 15 to about 30%; (v) $C_{16}$ ranging from about 5 to about 20%; (vi) $C_{18}$ ranging from about 1.5 to about 5%; and (vii) $C_{18}$ consisting of a combination of oleic and linoleic acids ranges from about 5 up to 7%.

According to one embodiment of the invention, there is provided a pearlescent concentrate containing: (a) from about 1 to about 25% by weight, and preferably from about 12 to about 15% by weight, of a pearlescent agent, (b) from about 2 to about 15% by weight, and preferably from about 4 to about 6% by weight, of a cocamide monoethanolamine, and (c) remainder, water, all weights being based on the total weight of the pearlescent concentrate.

The cocamide monoethanolamine preferably has a carbon chain distribution corresponding to: (i) $C_8$ of about 0.061%; (ii) $C_{10}$ of about 0.12%; (iii) $C_{12}$ of about 59.26%; (iv) $C_{14}$ of about 22.93%; (v) $C_{16}$ of about 10.18%; (vi) $C_{18}$ of about 1.83%; and (vii) $C_{18}$ consisting of a combination of oleic and linoleic acids of about 5.62%.

According to another embodiment of the present invention, there is provided a surfactant composition having enhanced pearlescent properties, the composition containing at least one surfactant component and from about 10 to about 75% by weight, and preferably from about 50 to about 55% by weight, based on the total weight of the composition, of the above-disclosed pearlescent concentrate.

The surfactant component, which is different from the pearlescent concentrate, may be selected from any of a wide variety of anionic, amphoteric, zwitterionic and nonionic surfactants, as well as mixtures thereof.

Anionic surfactants can be exemplified by the alkali metal salts of organic sulfuric reaction products having in their molecular structure an alkyl radical containing from 8–22 carbon atoms and a sulfonic acid or sulfuric acid ester radical (included in the term alkyl is the alkyl portion of higher acyl radicals).

Zwitterionic surfactants can be exemplified by those which can be broadly described as derivatives of aliphatic quaternary ammonium, phosphonium, and sulfonium compounds in which the aliphatic radicals can be straight chain or branched and wherein one of the aliphatic substituents contains from about 8 to 18 carbon atoms and one contains an anionic water-solubilizing group such as carboxyl, sulfonate, sulfate, phosphate or phosphonate.

Examples of amphoterics which may be used include those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate or phosphonate.

Nonionic surfactants which may be used can be broadly defined as compounds produced by the condensation of alkylene oxide groups (hydrophilic in nature) with an organic hydrophobic compound which may be aliphatic or alkyl aromatic in nature. Particularly preferred nonionic surfactants include the sugar surfactants such as alkyl polyglycoside and polyhydroxy fatty acid amides.

Optional ingredients which may also be employed in the surfactant composition of the present invention include, for example, preservatives, cationic surfactants, pH adjusting agents, perfumes, dyes, and sequestering agents.

According to yet another aspect of the present invention, there is provided a process for making a surfactant composition having enhanced pearlescent properties involving: (a) providing a surfactant composition containing at least one surfactant component, (b) providing an aqueous pearlescent concentrate containing a pearlescent agent and a cocamide monoethanolamine wherein the cocamide monoethanolamine has a carbon chain distribution corresponding to: (i) $C_8$ ranging from about 0.05 to about 2%, and preferably about 0.061%; (ii) $C_{10}$ ranging from about 0.1 to about 2%, and preferably about 0.12%; (iii) $C_{12}$ ranging from about 40 to about 70%, and preferably about 59.26%; (iv) $C_{14}$ ranging from about 15 to about 30%, and preferably about 22.93%; (v) $C_{16}$ ranging from about 5 to about 20%, and preferably about 10.18%; (vi) $C_{18}$ ranging from about 1.5 to about 5%, and preferably about 1.83%; and (vii) $C_{18}$ consisting of a combination of oleic and linoleic acids ranging from about 5 up to 7%, and preferably about 5.62%, and (c) mixing (a) and (b).

The present invention will be better understood from the examples which follow, all of which are meant to be illustrative only, and are not intended to limit the scope of the invention in any way.

EXAMPLES

Liquid pearlescent concentrates were formulated by combining those components contained in Table 1 below.

TABLE 1

| Component | Example 1 (% w/w) | Comp. Ex. 1 (% w/w) |
| --- | --- | --- |
| sodium laureth sulfate | 53.4 | 53.4 |
| fatty alcohol | 23.8 | 23.8 |
| pearl agent A | 5.8 | — |
| pearl agent B | — | 5.8 |
| glycol distearate | 13.6 | 13.6 |
| EDTA | 0.09 | 0.09 |
| sodium chloride | 0.38 | 0.38 |
| formaldehyde | 0.13 | 0.13 |
| citric acid | 0.04 | 0.04 |
| water | remainder to 100% | remainder to 100% |

Pearl agent A is a cocamide monoethanolamide commensurate in scope with the present invention. Pearl agent B is a cocamide monoethanolamide known in the art. The difference between the two pearl agents relates to their carbon-chain distributions, which are noted in Table 2, below.

TABLE 2

| C-chain distribution | Pearl agent A | Pearl agent B |
| --- | --- | --- |
| C8 | 0.061 | 0.10 |
| C10 | 0.12 | 0.99 |
| C12 | 59.26 | 57.51 |
| C14 | 22.93 | 19.20 |
| C16 | 10.18 | 8.80 |
| C18 | 1.83 | 2.74 |
| C18 (1 + 2)* | 5.62 | 10.66 |

*C18 (1 + 2) = a C18 carbon chain length distribution of a mixture of both oleic and linoleic acid.

The pearlescent concentrates of Table 1 were then used to formulate surfactant compositions, as is illustrated in Table 3 below.

TABLE 3

| Component | Example 1A (% w/w) | Comparative Ex. 1A (% w/w) |
| --- | --- | --- |
| sodium laureth sulfate | 40 | 40 |
| cocamidopropyl betaine | 5 | 5 |
| cocamide diethanolamide | 3 | 3 |
| sodium chloride | 1 | 1 |
| preservative | 0.05 | 0.05 |
| Example 1 pearlescent conc. | 2 | — |
| Example 2 pearlescent conc. | — | 2 |
| water | QS to 100 | QS to 100 |

The appearance of the composition formed by the above-formulated surfactant compositions was rated on a scale of 1 to 10 with 10 being the highest. The surfactant composition of Example 1A was rated a 10 while that of Comparative Examples 1A was a 1. The shampoo composition formed in Example 1A had a bright, rich, lustrous pearlescent layer appearance.

As can be seen from the results obtained, the pearlescent properties of a surfactant composition using the pearlescent concentrate of the present invention are much deeper and richer than those of conventional pearlescents. Also, due to the amplification of pearlescence provided by the use of the above-disclosed cocamide monoethanolamine, less pearlescent agent such as ethylene glycol mono- and distearate is required.

What is claimed is:

1. A pearlescent concentrate comprising:
   (a) from about 1 to about 25% by weight of a pearlescent agent;
   (b) from about 2 to about 15% by weight of a cocamide monoethanolamine having a carbon chain distribution corresponding to:
      (i) $C_8$ ranging from about 0.05 to about 2%;
      (ii) $C_{10}$ ranging from about 0.1 to about 2%;
      (iii) $C_{12}$ ranging from about 40 to about 70%;
      (iv) $C_{14}$ ranging from about 15 to about 30%;
      (v) $C_{16}$ ranging from about 5 to about 20%;
      (vi) $C_{18}$ ranging from about 1.5 to about 5%; and
      (vii) $C_{18}$ consisting of a combination of oleic and linoleic acids ranges from about 5 up to 7%; and
   (c) remainder, water, the weights of (a)–(c) being based on the total weight of the pearlescent concentrate.

2. The concentrate of claim 1 wherein the pearlescent agent is present in the concentrate in an amount of from about 12 to about 15% by weight, based on the weight of the concentrate.

3. The concentrate of claim 1 wherein the pearlescent agent is selected from the group consisting of ethylene glycol monostearate, ethylene glycol distearate, and mixtures thereof.

4. The concentrate of claim 1 wherein the cocamide monoethanolamine is present in the concentrate in an amount of from about 4 to about 6% by weight, based on the weight of the concentrate.

5. The concentrate of claim 1 wherein the carbon chain distribution of the cocamide monoethanolamine corresponds to:
   (i) $C_8$ of about 0.061%;
   (ii) $C_{10}$ of about 0.12%;
   (iii) $C_{12}$ of about 59.26%;
   (iv) $C_{14}$ of about 22.93%;
   (v) $C_{16}$ of about 10.18%;
   (vi) $C_{18}$ of about 1.83%; and
   (vii) $C_{18}$ consisting of a combination of oleic and linoleic acids of about 5.62%.

6. A surfactant composition comprising:
   (A) at least one surfactant; and
   (B) a pearlescent concentrate containing:
      (a) from about 1 to about 25% by weight of a pearlescent agent;
      (b) from about 2 to about 15% by weight of a cocamide monoethanolamine having a carbon chain distribution corresponding to:
         (i) $C_8$ ranging from about 0.05 to about 2%;
         (ii) $C_{10}$ ranging from about 0.1 to about 2%;
         (iii) $C_{12}$ ranging from about 40 to about 70%;
         (iv) $C_{14}$ ranging from about 15 to about 30%;
         (v) $C_{16}$ ranging from about 5 to about 20%;
         (Vi) $C_{18}$ ranging from about 1.5 to about 5%; and
         (vii) $C_{18}$ consisting of a combination of oleic and linoleic acids ranges from about 5 up to 7%; and
      (c) remainder, water, the weights of (a)–(c) being based on the total weight of the pearlescent concentrate.

7. The composition of claim 6 wherein the surfactant is selected from the group consisting of anionics, amphoterics, zwitterionics, nonionics, and mixtures thereof.

8. The composition of claim 6 wherein the pearlescent concentrate is present in the composition in an amount of from about 10 to about 75% by weight, based on the weight of the composition.

9. The composition of claim 6 wherein the carbon chain distribution of the cocamide monoethanolamine corresponds to:
   (i) $C_8$ of about 0.061%;
   (ii) $C_{10}$ of about 0.12%;
   (iii) $C_{12}$ of about 59.26%;
   (iv) $C_{14}$ of about 22.93%;
   (V) $C_{16}$ of about 10.18%;
   (vi) $C_{18}$ of about 1.83%; and
   (vii) $C_{18}$ consisting of a combination of oleic and linoleic acids of about 5.62%.

10. The composition of claim 6 wherein the pearlescent agent is selected from the group consisting of ethylene glycol monostearate, ethylene glycol distearate, and mixtures thereof.

11. A process for making a pearlescent surfactant composition comprising:
    (A) providing a surfactant composition;
    (B) providing an aqueous pearlescent concentrate containing:
       (a) a pearlescent agent; and
       (b) a cocamide monoethanolamine having a carbon chain distribution corresponding to:
          (i) $C_8$ ranging from about 0.05 to about 2%;
          (ii) $C_{10}$ ranging from about 0.1 to about 2%;
          (iii) $C_{12}$ ranging from about 40 to about 70%;
          (iv) $C_{14}$ ranging from about 15 to about 30%;
          (V) $C_{16}$ ranging from about 5 to about 20%;
          (vi) $C_{18}$ ranging from about 1.5 to about 5%; and
          (vii) $C_{18}$ consisting of a combination of oleic and linoleic acids ranges from about 5 up to 7%; and
    (C) mixing (A) and (B).

12. The process of claim 11 wherein the surfactant is selected from the group consisting of anionics, amphoterics, zwitterionics, nonionics, and mixtures thereof.

13. The process of claim 11 wherein the pearlescent concentrate is present in the composition in an amount of from about 10 to about 75% by weight, based on the weight of the composition.

14. The process of claim 11 wherein the carbon chain distribution of the cocamide monoethanolamine corresponds to:
    (i) $C_8$ of about 0.061%;
    (ii) $C_{10}$ of about 0.12%;
    (iii) $C_{12}$ of about 59.26%;
    (iv) $C_{14}$ of about 22.93%;
    (v) $C_{16}$ of about 10.18%;
    (vi) $C_{18}$ of about 1.83%; and
    (vii) $C_{18}$ consisting of a combination of oleic and linoleic acids of about 5.62%.

15. The process of claim 11 wherein the pearlescent agent is selected from the group consisting of ethylene glycol monostearate, ethylene glycol distearate, and mixtures thereof.

16. The product of the process of claim 11.
17. The product of the process of claim 12.
18. The product of the process of claim 13.
19. The product of the process of claim 14.
20. The product of the process of claim 15.

* * * * *